(12) United States Patent
Hagiya

(10) Patent No.: US 7,678,947 B2
(45) Date of Patent: Mar. 16, 2010

(54) METHOD FOR PRODUCING HALOGEN-SUBSTITUTED BENZENEDIMETHANOL

(75) Inventor: Koji Hagiya, Ibaraki (JP)

(73) Assignee: Sumitomo Chemical Company, Limited, Tokyo (JP)

( * ) Notice: Subject to any disclaimer, the term of this patent is extended or adjusted under 35 U.S.C. 154(b) by 178 days.

(21) Appl. No.: 11/572,505

(22) PCT Filed: Aug. 2, 2005

(86) PCT No.: PCT/JP2005/014486

§ 371 (c)(1),
(2), (4) Date: Jan. 23, 2007

(87) PCT Pub. No.: WO2006/013999

PCT Pub. Date: Feb. 9, 2006

(65) Prior Publication Data

US 2007/0213570 A1      Sep. 13, 2007

(30) Foreign Application Priority Data

Aug. 5, 2004    (JP) .............................. 2004-228954

(51) Int. Cl.
*C07C 33/28*     (2006.01)
*C07C 29/136*    (2006.01)
(52) U.S. Cl. ...................... 568/811; 568/814
(58) Field of Classification Search .................. 568/811, 568/814
See application file for complete search history.

(56) References Cited

U.S. PATENT DOCUMENTS

| 4,183,950 | A | 1/1980 | Naumann et al. |
| 4,927,852 | A | 5/1990 | Robson et al. |
| 5,583,131 | A | 12/1996 | Bridger et al. |
| 6,323,373 | B1 | 11/2001 | Spreitzer et al. |
| 6,759,558 | B2 | 7/2004 | Rodefeld |
| 6,909,023 | B2 | 6/2005 | Murakami et al. |
| 7,312,366 | B2 * | 12/2007 | Wang et al. .................. 568/811 |

FOREIGN PATENT DOCUMENTS

| CN | 1 458 137 A | 11/2003 |
| CN | 1458137 A | 11/2003 |
| EP | 1 182 184 A1 | 2/2002 |
| EP | 1 362 856 A1 | 11/2003 |
| EP | 1 428 813 A1 | 6/2004 |
| GB | 2 217 013 A | 4/1984 |
| JP | 61-218542 A | 9/1986 |
| JP | 11-43455 A | 2/1999 |
| JP | 2002-512593 A | 4/2002 |
| WO | WO 2005/035474 A1 | 4/2005 |

OTHER PUBLICATIONS

K. Soai et al, "Practical Procedure for the Chemoselective Reduction of Esters by Sodium Borohydride Effect of the Slow Addition to Methsnol[1])", The Chemical Society of Japan, Bull. Chem. Soc. Jpn., vol. 57, No. 7, (1984), pp. 1948-1953.
H. Brown et al, "Selective Reductions. 30. Effect of Cation and Solvent on the Reactivity of Saline Borohydrides for Reduction of Carboxylic Esters. Improved Procedures for the Conversion of Esters to Alcohols by Metal Borohydrides", J. Org. Chem. 47, (1982), pp. 4702-4708.

* cited by examiner

*Primary Examiner*—Sikarl A Witherspoon
(74) *Attorney, Agent, or Firm*—Sughrue Mion, PLLC

(57) ABSTRACT

A method for producing a halogen-substituted benzenedimethanol represented by the formula (2):

$$\begin{array}{c} CH_2OH \\ X^1 \diagup\diagdown X^2 \\ X^3 \diagdown\diagup X^4 \\ CH_2OH \end{array} \quad (2)$$

wherein $X^1$ to $X^4$ are the same or different and independently represent a halogen atom or the like, provided that at least one of $X^1$ to $X^4$ is a halogen atom, by reacting a halogen-substituted terephthalic acid diester represented by the formula (1):

$$\begin{array}{c} CO_2R^1 \\ X^1 \diagup\diagdown X^2 \\ X^3 \diagdown\diagup X^4 \\ CO_2R^2 \end{array} \quad (1)$$

wherein $R^1$ and $R^2$ are the same or different and independently represent a C1-C20 alkyl group which may have a substitutent or substituents, and $X^1$ to $X^4$ is the same as defined above,
with a borohydride compound in the presence of an alcohol which comprises adding the alcohol into a mixture of the halogen-substituted terephthalic acid diester represented by the formula (1), the borohydride compound and a solvent.

8 Claims, No Drawings

METHOD FOR PRODUCING HALOGEN-SUBSTITUTED BENZENEDIMETHANOL

TECHNICAL FIELD

The present invention relates to a method for producing a halogen-substituted benzenedimethanol.

BACKGROUND ART

A halogen-substituted benzenedimethanol is an important compound as raw materials and intermediates of pharmaceuticals and agrichemicals, and especially, U.S. Pat. No. 4,927,852 discloses 2,3,5,6-tetrafluorobenzenedimethanol is useful as an intermediate of household pesticides.

As a method for producing 2,3,5,6-tetrafluorobenzenedimethanol, for example, U.S. Pat. No. 4,927,852 discloses a method comprising conducting bromination of 2,3,5,6-tetrafluoroparaxylene followed by conducting acetoxylation and then hydrolysis. GB 2127013 A discloses a method comprising reacting 2,3,5,6-tetrafluoroterephthalic chloride with sodium borohydride. U.S. Pat. No. 5,583,131 discloses a method comprising reacting 2,3,5,6-tetrafluoroterephthalic acid with borane-tetrahydrofuran complex and U.S. Pat. No. 6,759,558 discloses a method comprising reacting 2,3,5,6-tetrafluoroterephthalic acid with sodium borohydride in the presence of dimethyl sulfate or sulfuric acid. JP 2002-20332 A discloses a method comprising hydrogenating 2,3,5,6-tetrafluoroterephthalonitrile followed by conducting diazotization and then hydrolysis.

DISCLOSURE OF THE INVENTION

The present invention provides a method for producing a halogen-substituted benzenedimethanol represented by the formula (2):

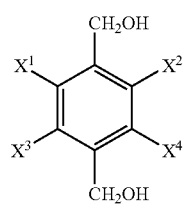

(2)

wherein $X^1$ to $X^4$ are the same or different and independently represent a hydrogen or halogen atom, provided that at least one of $X^1$ to $X^4$ is a halogen atom, by reacting a halogen-substituted terephthalic acid diester represented by the formula (1):

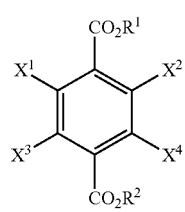

(1)

wherein $R^1$ and $R^2$ are the same or different and independently represent an optionally substituted C1-C20 alkyl group and the substitutent of the alkyl group is a fluorine atom; a C1-C20 alkoxy group which is optionally substituted with a halogen atom or atoms; a C6-C20 aryl group which is optionally substituted with a C1-C6 alkoxy group or groups; a C6-C20 aryloxy group which is optionally substituted with a C1-C6 alkoxy group or groups or phenoxy group or groups; or a C7-C20 aralkyloxy group which is optionally substituted with a C1-C6 alkoxy group or groups or phenoxy group or groups, and $X^1$ to $X^4$ is the same as defined above, with a borohydride compound in the presence of an alcohol which comprises adding the alcohol into a mixture of the halogen-substituted terephthalic acid diester represented by the formula (1), the borohydride compound and a solvent.

BEST MODE FOR CARRYING OUT THE PRESENT INVENTION

In the halogen-substituted terephthalic acid diester represented by the formula (1) (hereinafter, simply referred to as the halogen-substituted terephthalic acid diester (1)), in the formula, $R^1$ and $R^2$ are the same or different and represent a C1-C20 alkyl group which may have a substituent or substituents. Herein, the above-mentioned substituent is a fluorine atom; a C1-C20 alkoxy group which is optionally substituted with a halogen atom or atoms; a C6-C20 aryl group which is optionally substituted with a C1-C6 alkoxy group or groups; a C6-C20 aryloxy group which is optionally substituted with a C1-C6 alkoxy group or groups or a phenoxy group or groups; or a C7-C20 aralkyloxy group which is optionally substituted with a C1-C6 alkoxy group or groups or phenoxy group or groups. $X^1$ to $X^4$ are the same or different and independently represent a hydrogen or halogen atom, provided that at least one of $X^1$ to $X^4$ is a halogen atom.

Examples of the C1-C20 alkyl group include a straight chain, branched chain or cyclic alkyl group such as a methyl, ethyl, n-propyl, isopropyl, n-butyl, isobutyl, sec-butyl, tert-butyl, n-pentyl, n-decyl, cyclopropyl, 2,2-dimethylcyclopropyl, cyclopentyl, cyclohexyl and menthyl group.

The alkyl group may have a substituent or substituents and the substituent is a fluorine atom; a C1-C20 alkoxy group which is optionally substituted with a halogen atom or atoms; a C6-C20 aryl group which is optionally substituted with a C1-C6 alkoxy group or groups; a C6-C20 aryloxy group which is optionally substituted with a C1-C6 alkoxy group or groups or a phenoxy group or groups; or a C7-C20 aralkyloxy group which is optionally substituted with a C1-C6 alkoxy group or groups or phenoxy group or groups.

Examples of the halogen atom include a fluorine, chlorine and bromine atom.

Examples of the C1-C20 alkoxy group which is optionally substituted with a halogen atom or atoms include a methoxy, ethoxy, n-propoxy, isopropoxy, n-butoxy, isobutoxy, sec-butoxyl, tert-butoxy, n-hexyloxy, n-decyloxy and trifluoromethoxy group.

Examples of the C6-C20 aryl group which is optionally substituted with a C1-C6 alkoxy group or groups include a phenyl, 4-methylphenyl and 4-methoxyphenyl group.

Examples of the C6-C20 aryloxy group which is optionally substituted with a C1-C6 alkoxy group or groups or a phenoxy group or groups include a phenoxy, 2-methylphenoxy, 4-methylphenoxy, 4-methoxyphenoxy and 3-phenoxyphenoxy group.

Examples of the C7-C20 aralkyloxy group which is optionally substituted with a C1-C6 alkoxy group or groups or a phenoxy group or groups include a benzyloxy, 4-methylbenzyloxy, 4-methoxybenzyloxy and 3-phenoxybenzyloxy group.

Examples of the alkyl group substituted with the substituent or substituents include a fluoromethyl, trifluoromethyl, methoxymethyl, ethoxymethyl, methoxyethyl, benzyl, phenoxymethyl and benzyloxymethyl group.

Examples of the halogen-substituted terephthalic acid diester (1) include dimethyl 2-fluoroterephthalate, dimethyl 2-chloroterephthalate, dimethyl 2,5-difluoroterephthalate, dimethyl 2,6-difluoroterephthalate, dimethyl 2,3-difluoroterephthalate, dimethyl 2,5-dichloroterephthalate, dimethyl 2,6-dichloroterephthalate, dimethyl 2,3-dichloroterephthalate, dimethyl 2,3,5-trifluoroterephthalate, dimethyl 2,3,5-trichloroterephthalate, dimethyl 2,3,5,6-tetrafluoroterephthalate, diethyl 2,3,5,6-tetrafluoroterephthalate, di(n-propyl) 2,3,5,6-tetrafluoroterephthalate, diisopropyl 2,3,5,6-tetrafluoroterephthalate, di(n-butyl) 2,3,5,6-tetrafluoroterephthalate, di(tert-butyl) 2,3,5,6-tetrafluoroterephthalate, dimethyl 2,3,5,6-tetrachloroterephthalate, diethyl 2,3,5,6-tetrachloroterephthalate, di(n-propyl) 2,3,5,6-tetrachloroterephthalate, diisopropyl 2,3,5,6-tetrachloroterephthalate, di(n-butyl) 2,3,5,6-tetrachloroterephthalate, di(tert-butyl) 2,3,5,6-tetrachloroterephthalate, and dimethyl 2,3,5-trifluoro-6-chloroterephthalate. The halogen-substituted terephthalic acid diester (1) wherein $R^1$ and $R^2$ are the same C1-C6 alkyl groups is preferable.

The halogen-substituted terephthalic acid diester (1) can be produced, for example, by a method described in EP 0140482 B.

Examples of the borohydride compound include an alkali metal borohydride such as sodium borohydride, lithium borohydride and potassium borohydride and an alkaline earth metal borohydride such as calcium borohydride and magnesium borohydride. The alkali metal borohydride is preferable and sodium borohydride is more preferable.

A commercially available borohydride compound may be used and those prepared according to method described in U.S. Pat. No. 3,471,268, Inorganic Chemistry, 1981, 20, 4454 and the like may be used. As the borohydride compound, those priviously prepared may be used and it may be prepared in the reaction system.

The amount of the borohydride compound to be used is usually 2 to 5 moles, preferably 2 to 2.5 moles relative to 1 mole of the halogen-substituted terephthalic acid diester (1).

The alcohol means an organic compound wherein one or more hydrogen atom of a hydrocarbon is substituted with a hydroxyl group. Examples thereof include an aliphatic alcohol such as methanol, ethanol, n-propanol, isopropanol, n-butanol and tert-butanol, and an aromatic alcohol such as phenol and benzyl alcohol, and the aliphatic alcohol is preferable and methanol is more preferable. The amount of the alcohol to be used is not particularly limited and large excess thereof, for example, 100 parts by weight relative to 1 part of the halogen-substituted terephthalic acid diester (1), may be used as the solvent and it is practically 1 to 50 moles relative to 1 mole of the halogen-substituted terephthalic acid diester (1).

The present reaction is carried out in a solvent. Examples of the solvent include an ether solvent such as diethyl ether, methyl tert-butyl ether, tetrahydrofuran, dioxane and diisopropyl ether, and an aromatic hydrocarbon solvent such as toluene, xylene and chlorobenzene. The alcohol can be used as the solvent as described above. The amount of the solvent to be used is not particularly limited and it is practically not more than 100 parts by weight relative to 1 part of the halogen-substituted terephthalic acid diester (1).

The reaction is conducted by adding the alcohol to a mixture obtained by mixing the halogen-substituted terephthalic acid diester (1), the borohydride compound and the solvent.

The reaction is usually carried out under ordinary pressure conditions, and may be carried out under pressurized conditions. The progress of the reaction can be confirmed by a conventional analytical means such as gas chromatography and high performance liquid chromatography.

After completion of the reaction, for example, a reaction liquid is mixed with an aqueous solution of a mineral acid such as hydrochloric acid, sulfuric acid, phosphoric acid and nitric acid, if necessary, followed by conducting treatment such as neutralizing, extracting using an organic solvent and concentrating to isolate a halogen-substituted benzenedimethanol represented by the formula (2) (hereinafter, simply referred to as the halogen-substituted benzenedimethanol (2)). The halogen-substituted benzenedimethanol (2) isolated may be further purified by a conventional purification means such as recrystallization and column chromatography.

Examples of the halogen-substituted benzenedimethanol (2) thus obtained include 2-fluoro-1,4-benzendimethanol, 2-chloro-1,4-benzendimethanol, 2,5-difluoro-1,4-benzendimethanol, 2,6-difluoro-1,4-benzendimethanol, 2,3-difluoro-1,4-benzendimethanol, 2,5-dichloro-1,4-benzendimethanol, 2,6-dichloro-1,4-benzendimethanol, 2,3-dichloro-1,4-benzendimethanol, 2,3,5-trifluoro-1,4-benzendimethanol, 2,3,5-trichloro-1,4-benzendimethanol, 2,3,5,6-tetrafluorobenzendimethanol, 2,3,5,6-tetrachlorobenzendimethanol, and 2,3,5-trifluoro-6-chlorobenzendimethanol.

EXAMPLES

Example 1

Into a 200 ml flask, 2.61 g of sodium borohydride, 26.8 g of tetrahydrofuran and 8.94 g of dimethyl 2,3,5,6-tetrafluoroterephthalate were charged. 26.7 g of methanol was added dropwise thereto at an inner temperature of 55° C. over 80 minutes with stirring. After stirring at the same temperature for 6.5 hours, the mixing was conducted at room temperature for 20 hours. 24.5 g of 10% by weight hydrochloric acid was added dropwise to the reaction liquid at 25 to 30° C. over 1 hour followed by stirring at the same temperature for 1 hour. Further, 8 g of 23% by weight aqueous sodium hydroxide was added thereto. The solution obtained was concentrated, 100 g of water was added to the residue obtained to extract three times with 70 g of ethyl acetate and the organic layers obtained were mixed. To the organic layer, magnesium sulfate anhydride was added and dried. After filtering off magnesium sulfate, the filtrate was concentrated to obtain 6.38 g of white crystals of 2,3,5,6-tetrafluorobenzenedimethanol. The crystals were analyzed by the gas chromatography internal standard method to find that the content of 2,3,5,6-tetrafluorobenzenedimethanol was 92.5%. Yield: 84%.

Example 2

Into a 200 ml flask, 1.66 g of sodium borohydride, 20 g of methyl tert-butyl ether and 5.32 g of dimethyl 2,3,5,6-tetrafluoroterephthalate were charged. 18.0 g of methanol was added dropwise thereto at an inner temperature of 55° C. over 3 hours with stirring. After stirring at the same temperature for 5 hours, the resultant mixture was cooled to room temperature. 16 g of 10% by weight hydrochloric acid was added dropwise to the reaction liquid at 25 to 30° C. over 30 minutes followed by stirring at the same temperature for 30 minutes.

Further, 45% by weight aqueous sodium hydroxide was added thereto to adjust to pH 8. Methanol and methyl tert-butyl ether were distilled away from the solution obtained and 50 g of ethyl acetate was added to the residue obtained to extract twice and the organic layers obtained were mixed. To the organic layer, magnesium sulfate anhydride was added and dried. After filtering off magnesium sulfate, the filtrate was concentrated to obtain 10 g of concentrated liquid. To the concentrated liquid, 30 g of toluene was added and the crystals were precipitated. The crystals was filtered and dried to obtain 3.82 g of white crystals of 2,3,5,6-tetrafluorobenzenedimethanol. The crystals were analyzed by the liquid chromatography area percentage method to find that the content of 2,3,5,6-tetrafluorobenzenedimethanol was 95.5%. Yield: 87%.

Example 3

Into a 200 ml flask, 1.66 g of sodium borohydride, 18 g of tetrahydrofuran and 6.64 g of dimethyl 2,3,5,6-tetrachloroterephthalate were charged. 18.0 g of methanol was added dropwise thereto at an inner temperature of 55° C. over 3 hours with stirring. After stirring at the same temperature for 5 hours, the resultant mixture was cooled to room temperature. 16 g of 10% by weight hydrochloric acid was added dropwise to the reaction liquid at 25 to 30° C. over 30 minutes followed by stirring at the same temperature for 30 minutes. Further, 45% by weight aqueous sodium hydroxide was added thereto to adjust to pH 8. Methanol and tetrahydrofuran were distilled away from the solution obtained, and 50 g of ethyl acetate was added to the residue obtained to repeat twice extraction and the organic layers obtained were mixed. To the organic layer, magnesium sulfate anhydride was added to conduct dehydration and then, the solid was filtering off. The filtrate was concentrated and to the residue obtained, 5 g of toluene and 30 g of n-hexane were added and the crystals were precipitated. The crystals was filtered and dried to obtain 4.40 g of white crystals of 2,3,5,6-tetrachlorobenzenedimethanol. The crystals were analyzed by the liquid chromatography area percentage method to find that the content of 2,3,5,6-tetrachlorobenzenedimethanol was 99.6%. Further, the filtrate after filtering the crystals was concentrated and the crystals precipitated were filtered and dried to obtain 0.63 g of white crystals of 2,3,5,6-tetrachlorobenzenedimethanol. The content of 2,3,5,6-tetrachlorobenzenedimethanol was 90.2%. Yield: 90%.

What is claimed is:

1. A method for producing a halogen-substituted benzenedimethanol represented by the formula (2):

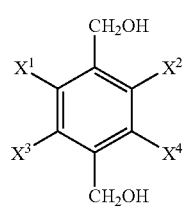

(2)

wherein $X^1$ to $X^4$ are the same or different and independently represent a hydrogen or halogen atom, provided that at least one of $X^1$ to $X^4$ is a halogen atom, by reacting a halogen-substituted terephthalic acid diester represented by the formula (1):

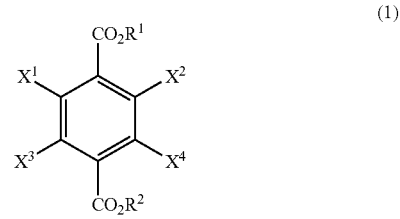

(1)

wherein $R^1$ and $R^2$ are the same or different and independently represent an optionally substituted C1-C20 alkyl group and the substituent of the alkyl group is a fluorine atom; a C1-C20 alkoxy group which is optionally substituted with a halogen atom or atoms; a C6-C20 aryl group which is optionally substituted with a C1-C6 alkoxy group or groups; a C6-C20 aryloxy group which is optionally substituted with a C1-C6 alkoxy group or groups or phenoxy group or groups; or a C7-C20 aralkyloxy group which is optionally substituted with a C1-C6 alkoxy group or groups or phenoxy group or groups, and $X^1$ to $X^4$ is the same as defined above, with a borohydride compound in the presence of an alcohol which comprises adding the alcohol into a mixture of the halogen-substituted terephthalic acid diester represented by the formula (1), the borohydride compound and a solvent.

2. The method according to claim 1, wherein $R^1$ and $R^2$ are the same C1-C6 alkyl groups.

3. The method according to claim 1 or 2, wherein all of $X^1$ to $X^4$ are fluorine atoms.

4. The method according to claim 1 or 2, wherein the amount of the borohydride compound to be used is 2 to 2.5 moles relative to 1 mole of the halogen-substituted terephthalic acid diester represented by the formula (1).

5. The method according to claim 1 or 2, wherein the borohydride compound is an alkali metal borohydride.

6. The method according to claim 5, wherein the alkali metal borohydride is sodium borohydride.

7. The method according to claim 1 or 2, wherein the alcohol is an aliphatic alcohol.

8. The method according to claim 7, wherein the aliphatic alcohol is methanol.

* * * * *